(12) United States Patent
Vanpoucke

(10) Patent No.: US 9,757,562 B2
(45) Date of Patent: Sep. 12, 2017

(54) FITTING METHOD USING TOKENS

(71) Applicant: Cochlear Limited, Macquarie University, NSW (AU)

(72) Inventor: Filiep J. Vanpoucke, Huldenberg (BE)

(73) Assignee: Cochlear Limited, Macquarie University, NSW (AU)

(*) Notice: Subject to any disclaimer, the term of this patent is extended or adjusted under 35 U.S.C. 154(b) by 0 days.

(21) Appl. No.: 14/958,368

(22) Filed: Dec. 3, 2015

(65) Prior Publication Data
US 2016/0158547 A1    Jun. 9, 2016

Related U.S. Application Data

(60) Provisional application No. 62/087,443, filed on Dec. 4, 2014.

(51) Int. Cl.
*A61N 1/00*    (2006.01)
*A61N 1/36*    (2006.01)
*A61B 5/12*    (2006.01)

(52) U.S. Cl.
CPC .......... *A61N 1/36032* (2013.01); *A61B 5/121* (2013.01)

(58) Field of Classification Search
CPC ............ A61N 1/36032; A61N 1/36132; A61N 1/36128
See application file for complete search history.

(56) References Cited

U.S. PATENT DOCUMENTS

2005/0055069 A1* 3/2005 Franck ..................... A61N 1/08
607/62

FOREIGN PATENT DOCUMENTS

EP    1338301 A1    8/2003

OTHER PUBLICATIONS

Govaerts et al., "Development of a Software Tool Using Deterministic Logic for the Optimization of Cochlear Implant Processor Programming," Otology & Neurotology, 2010, Otology & Neurotology, Inc.
Vaerenberg et al., "Experiences of the use of FOX, an intelligent agent, for programming cochlear implant sound processors in new users," International Journal of Audiology, 2010.

* cited by examiner

*Primary Examiner* — Scott Getzow
(74) *Attorney, Agent, or Firm* — Hauptman Ham, LLP

(57) ABSTRACT

A method, including obtaining data indicative of an ability of a recipient of a hearing prosthesis to discriminate between tokens of respective token pairs of a plurality of token pairs in respective evoked hearing percepts induced by the hearing prosthesis and adjusting one or more but less than all frequency channels of a plurality of frequency channels of the hearing prosthesis based on the obtained data.

24 Claims, 13 Drawing Sheets

FITTING METHOD USING TOKENS

CROSS-REFERENCE TO RELATED APPLICATIONS

This application claims priority to Provisional U.S. Patent Application No. 62/087,443, entitled FITTING METHOD USING TOKENS, filed on Dec. 4, 2014, naming Filiep J. Vanpoucke of Belgium as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In accordance with an exemplary embodiment, there is a method, comprising obtaining data indicative of an ability of a recipient of a hearing prosthesis to discriminate between tokens of respective token pairs of a plurality of token pairs in respective evoked hearing percepts induced by the hearing prosthesis, and adjusting one or more, but less than all frequency channels of a plurality of frequency channels of the hearing prosthesis based on the obtained data.

In accordance with another exemplary embodiment, there is a method of fitting a hearing prosthesis, comprising obtaining respective signal strength data for respective frequency bands for one or more first token pairs, the one or more first token pairs corresponding to hearing percepts evoked by the hearing prosthesis, identifying one or more frequency bands of the plurality of frequency bands for the one or more first token pairs where the respective signal strength data indicates relatively higher signal strength relative to that of one or more other frequency bands for the one or more token pairs, and adjusting parameters of the hearing prosthesis based on the identified frequency bands.

In accordance with another exemplary embodiment, there is a non-transitory computer readable medium having recorded thereon, a computer program for executing a method, program including code for manipulating frequency based data based on an ability of the recipient to correctly distinguish between tokens of the respective tokens, wherein the manipulated frequency based data is frequency based data for respective tokens of respectively evoked hearing percepts induced by a hearing prosthesis and code for adjusting an output control of the hearing prosthesis with respect to one or more frequency bands of a plurality of frequency bands of the hearing prosthesis based on the manipulated data.

BRIEF DESCRIPTION OF THE DRAWINGS

Embodiments are described below with reference to the attached drawings, in which.

DETAILED DESCRIPTION

Figure 1:
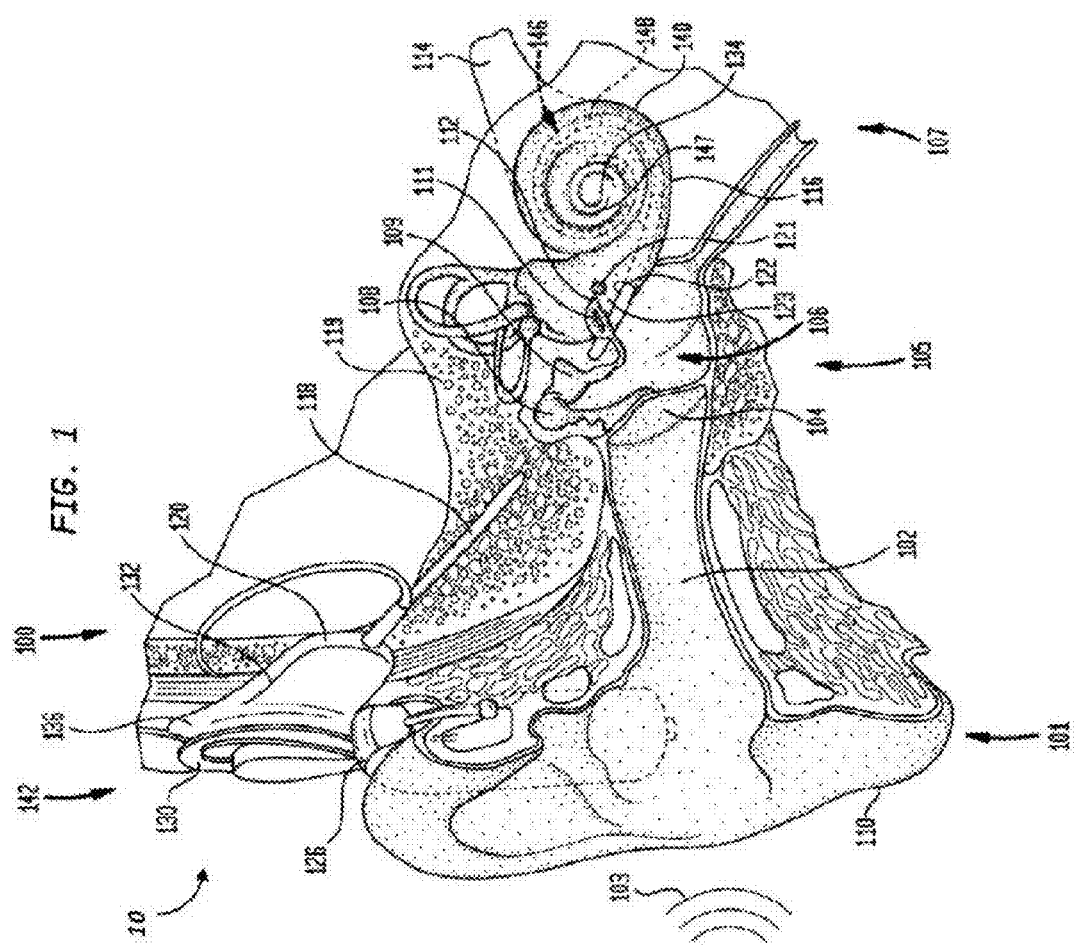
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components, in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.).

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery or other energy storage device (e.g., capacitor) that is charged (e.g., recharged) by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Because the cochlea is tonotopically mapped (i.e., spatial locations that are responsive to stimulus signals in a particular frequency range are identified), frequencies may be allocated to one or more electrodes of the electrode assembly to generate an electric field in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit of the BTE 126 (i.e., specific frequency bands with their associated signal processing paths), are mapped to a set of one or more electrodes to stimulate a desired nerve fiber or nerve region of the cochlea. Such sets of one or more electrodes for use in stimulation are referred to herein as "electrode channels" or "stimulation channels." In at least some exemplary embodiments, each channel has a "base" electrode corresponding to the electrode of the electrode array that is proximate the tonotopically mapped cochlea for a given frequency or frequency range.

Figure 2:
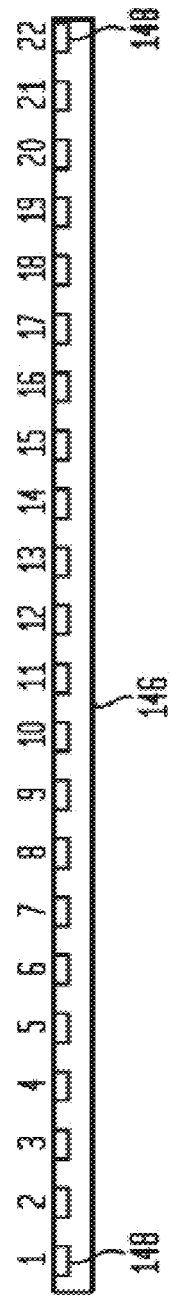
FIG. 2 presents an exemplary electrode array according to an exemplary embodiment.

FIG. 2 illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel) as will be discussed in greater detail below. Briefly, it is noted that during stimulation by the electrodes to evoke a hearing percept, one or more electrodes 148 is activated at a given electrode stimulation level (e.g., current level). This electrode stimulation level is pre-set during a fitting process. For example, in at least some instances, an audiologist adjusts stimulation channel electrode current levels of the cochlear implant 100 based on empirical data. More specifically, in at least some embodiments, stimulation channel electrode current levels are adjusted by an audiologist based on threshold and comfort levels. Then, in at least some embodiments, the cochlear implant 100 is configured such that respective stimulation channels of the cochlear implant 100 have those respective current levels. This can be done, for example, by programming the cochlear implant 100 or by any other process that sets the channels of the cochlear implant 100 to have the pertinent electrical stimulation levels. Any arrangement of the cochlear implant 100 and/or other equipment/devices that will enable the teachings detailed herein and/or variations thereof to be practiced can be used in at least some embodiments.

In view of this, an exemplary embodiment entails a fitting method that entails setting or otherwise adjusting the parameters of the cochlear implant 100 determining the electrical mapping from sound levels in one or more or all of the frequency bands to electrical stimulation levels. This exemplary fitting method can include an audiologist or other clinical professional turning the electrical map parameters of the cochlear implant 100 to the particular auditory physiology of the recipient. More specifically, this exemplary fitting method includes a feature that can be generally characterized as applied in at least some embodiments as a quality check on the adequateness of the map parameters for conversational and/or loud levels by obtaining data from a test that entails having the recipient discriminate between sounds.

Figure 3:
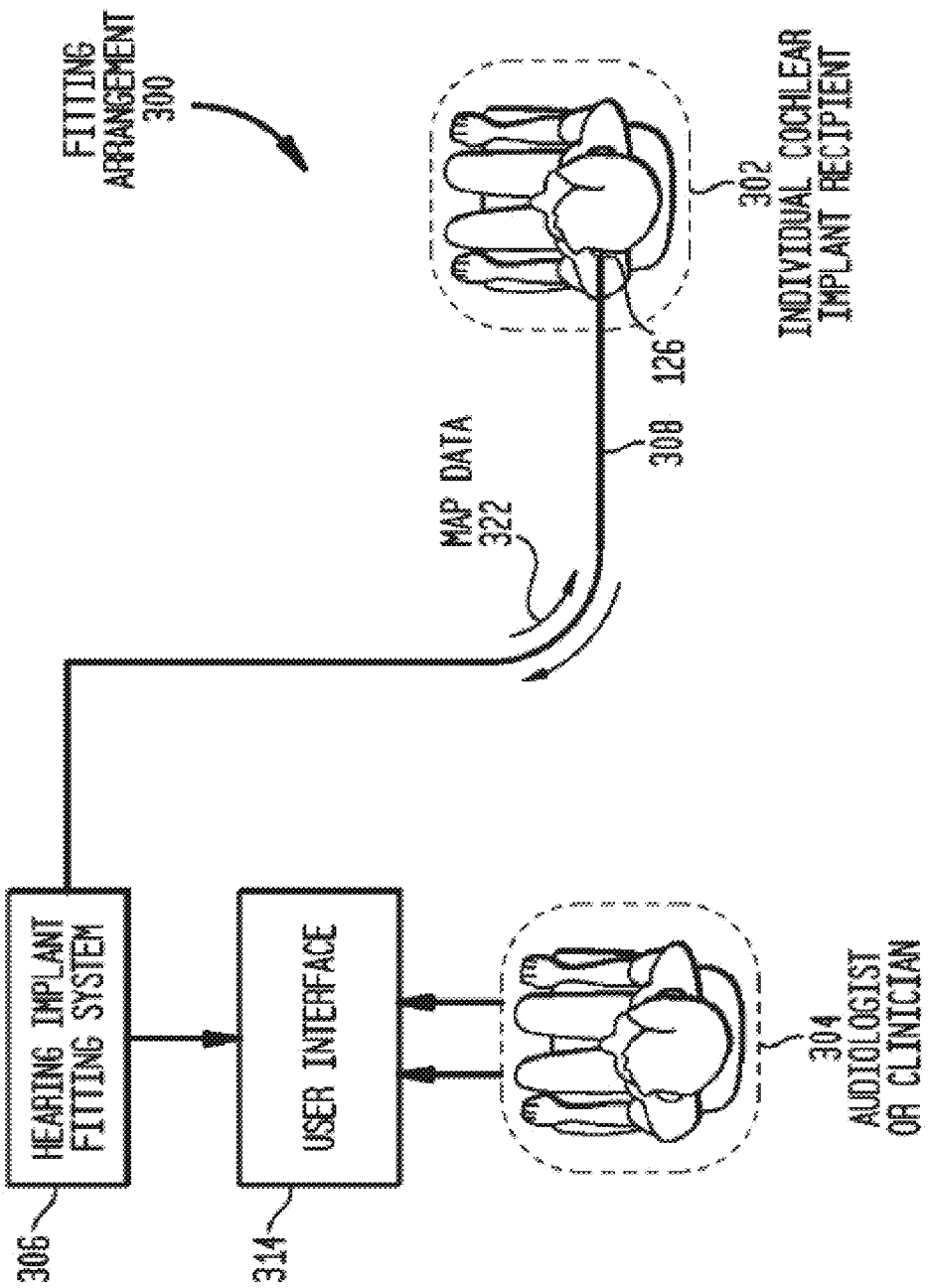
FIG. 3 presents an exemplary device in use according to an exemplary embodiment.

FIG. 3 is a schematic diagram illustrating one exemplary arrangement 300 in which a hearing implant fitting system 306 may be used to fit a cochlear implant, in accordance with an embodiment. As shown in FIG. 3, an audiologist or clinician 304 may use a hearing implant fitting system 306 ("fitting system" herein) comprising interactive software and computer hardware to create individualized recipient map data 322 that are digitally stored on system 306 and ultimately downloaded to the memory of the sound processing unit 126 for recipient 302. System 306 may be programmed and/or implement software programmed to carry out one or more of the functions of mapping, neural response measuring, acoustic stimulating, and recording of neural response measurements and other stimuli.

In the embodiment illustrated in FIG. 3, sound processing unit 126 of cochlear implant 100 may be connected directly to fitting system 306 to establish a data communication link 308 between the sound processing unit 126 and fitting system 306. System 306 is thereafter bi-directionally coupled by a data communication link 308 with sound processing unit 126. It should be appreciated that although sound processing unit 126 and fitting system 306 are connected via a cable in FIG. 3, any communications link now or later developed may be utilized to communicably couple the implant and fitting system.

Briefly, it is noted that the aforementioned quality check can be part of a fitting method, or can be separate from a fitting method (although it might more accurately be considered a second, separate fitting method). More specifically, the cochlear implant 100 (or other hearing prosthesis) can be fitted according to any method now known or to be developed that can enable the cochlear implant to be fitted. The teachings detailed herein can be added to those fitting methods, either as an expansion of those fitting methods, or as a separate fitting method.

As noted above, exemplary embodiments according to the teachings detailed herein utilize a test that gauges a recipient's ability (or inability) to detect differences/discriminate between sounds. In an exemplary embodiment, the sounds are stationary phonemes. In an alternate embodiment, the sounds can be synthetic vowels, psychoacoustic signals (e.g., spectral ripples, tones, etc.), short words (or long words, if such will enable the teachings detailed herein and/or variations thereof) and/or musical notes. That said, in an exemplary embodiment, the sounds are sounds that correspond to the core elements of any given language. Accordingly, in an exemplary embodiment, the teachings detailed herein and/or variations thereof can be applicable to recipients speaking a wide variety of languages without modification to a given fitting method.

Hereinafter, the aforementioned sounds (e.g., phonemes, etc.) are referred to as "tokens." An exemplary embodiment pairs different tokens and presents those tokens to the recipient utilizing a hearing prosthesis (such as the cochlear implant 100) to evoke a hearing percept having those different token pairs therein. An exemplary embodiment of the teachings detailed herein utilize the aforementioned pairs of different tokens to obtain information that can enable an audiologist or other clinical professional to adapt the map of the hearing prosthesis such that the recipient will be able to more effectively discriminate between tokens. This can be done by identifying one or more electrodes of the cochlear implant where a change in the map parameters can have utilitarian value.

Figure 4A:
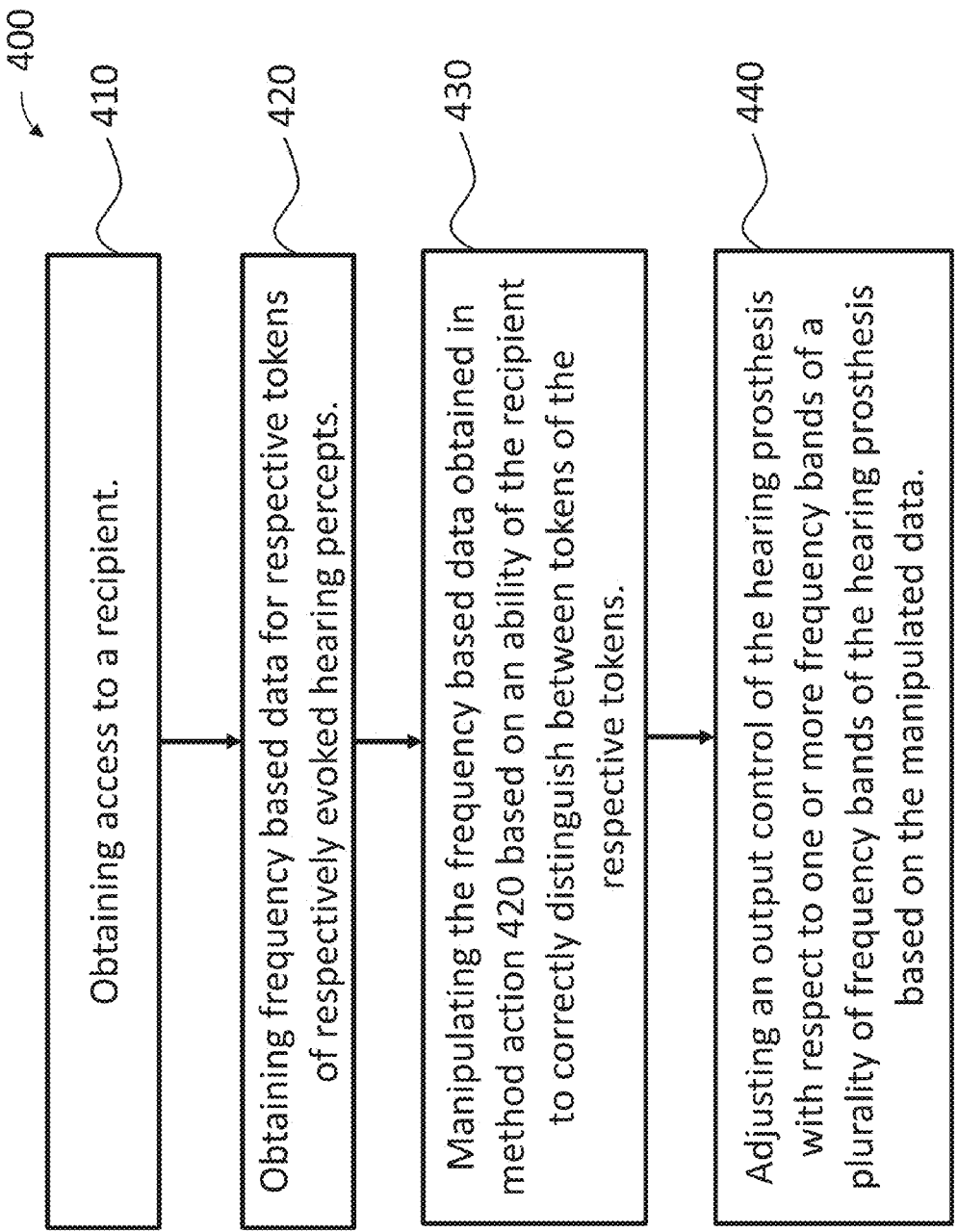
FIG. 4A presents an exemplary flowchart for an exemplary algorithm according to an exemplary embodiment.
Figure 4B:
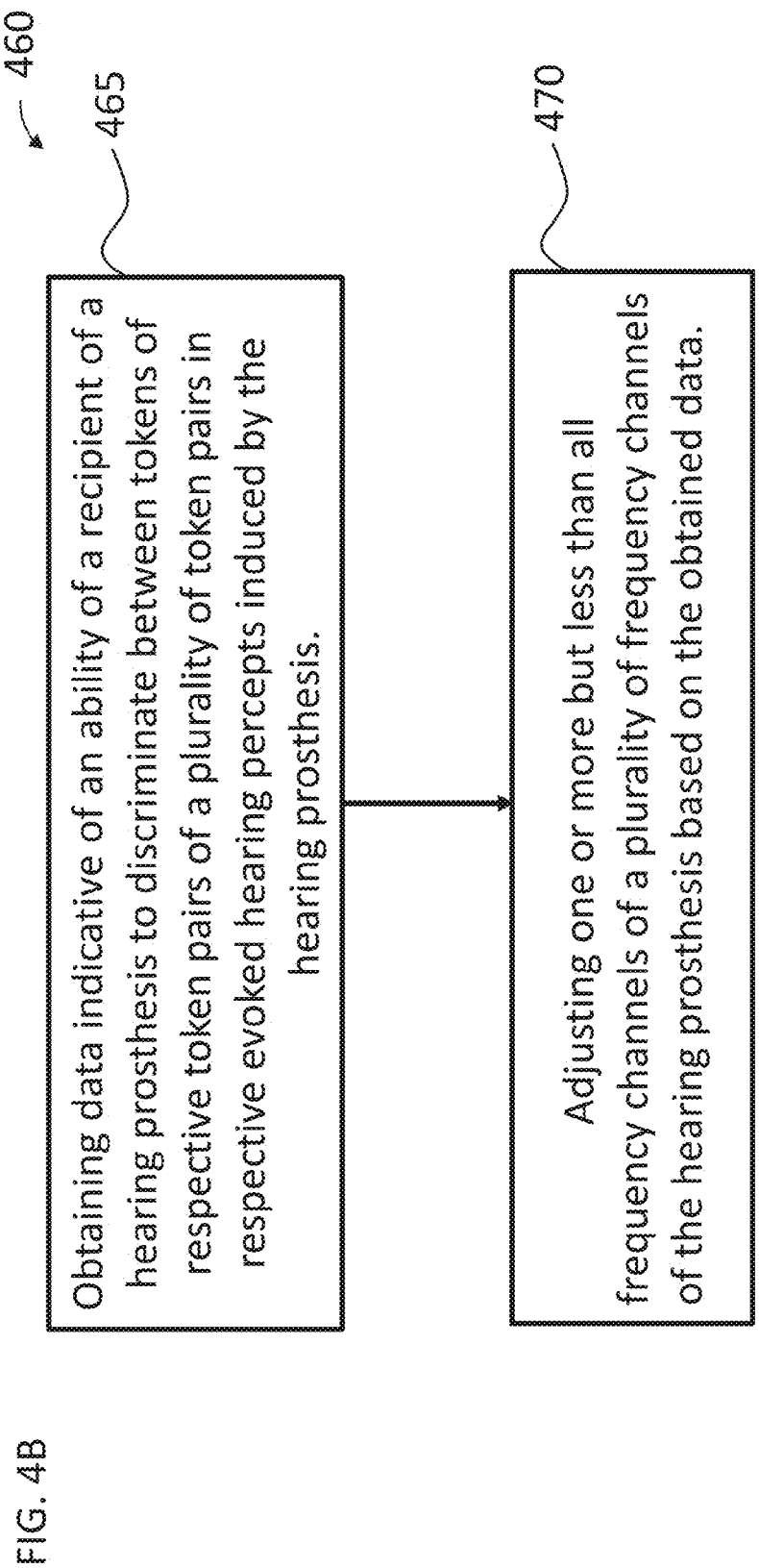
FIG. 4B presents another exemplary flowchart for an exemplary algorithm according to an exemplary embodiment.

Referring now to FIG. 4A, there is an exemplary flowchart 400 for a method including method actions 410, 420, 430 and 440. Also, in the following discussion, reference will be made to FIG. 4B, which presents another exemplary flowchart 460, also for a method that entails method actions 465 and 470. It is noted that the methods of FIGS. 4A and 4B are intertwined, in that in executing the method flowchart 400, in some embodiments, one or more method actions of method 460 will be executed. Indeed, in some embodiments, method 400 and method 460 are fully executed in a temporally overlapping manner (one method may begin and/or end before the other). Also, it is noted that other methods can be executed while executing the methods of FIGS. 4A and/or 4B. That said, some embodiments entail executing one method without executing the other (in part and/or in full).

Accordingly, the following discussion will variously reference method 400 and method 460 as appropriate.

Method action 410 entails obtaining access to a recipient having a plurality of electrodes of a cochlear implant implanted in the recipient, where the cochlear implant is at least partially fitted. That said, method action 410 can also include actually partially fitting the recipient. More specifically, in an exemplary embodiment, subsequent implantation of the cochlear implant 100 into the recipient, a method is executed to at least partially customize the cochlear implant 100 to conform to recipient desires/an operational configuration that is deemed desirable to the recipient of the cochlea implant 100. This procedure entails, in an exemplary embodiment, collecting information and determine patient specific parameters such as threshold levels (T levels) and maximum comfort levels (C levels) for one or more or all stimulation channels of the cochlear implant 100, and then setting (at least temporally), a map of the cochlear implant. This can be done, for example, by programming the cochlear implant 100 or by any other process that sets the channels of the cochlear implant 100 to have the map. That said, in an alternate embodiment, the cochlear implant 100 is not programmed or otherwise configured such that the channels of the cochlear implant 100 have a map before implementing the quality check/adjustment methods detailed herein. Instead, the map is stored in the fitting system used to fit the cochlear implant 100 and the quality check/adjustments are then executed, and then the cochlear implant 100 is configured such that the respective stimulation channels have the respective electrical stimulation levels adjusted based on the quality check.

In an exemplary embodiment, the recipient can correspond to a recipient having the anatomical structure present in FIG. 1 above who also has the cochlear implant 100 implanted therein, where the cochlear implant 100 is configured to apply electrical stimulation to the recipient via the plurality of electrodes by activating a plurality of stimulation channels. In an exemplary embodiment, an audiologist or the like executes method action 410 using the arrangement of FIG. 3. It is noted that method action 410 can be performed in-person (e.g., the audiologist and the recipient are at the same location) or, in other embodiments, can be performed remotely (e.g., the audiologist is remote from the recipient, the audiologist obtaining access to the recipient via, for example, an internet or phone link, etc.).

Method action 420 entails obtaining frequency based data for respective tokens of respectively evoked hearing percepts induced by a hearing prosthesis. In an exemplary embodiment, this can entail implementing an empirical process by which the electrical stimulation levels for respective frequency bands is obtained by evoking hearing percept using the cochlear implant 100, for a given token. Accordingly, in an exemplary embodiment, the obtained frequency based data corresponds to respective signal strengths for respective frequency bands (channels) of the cochlear implant.

This can be repeated a number of times for respective tokens. By way of example only and not by way of limitation, if four (4) tokens are to be utilized in a given method, this would be repeated four times for the four tokens.

In an exemplary embodiment, an odd man out method is used where a test token is immersed in a sequence of reference tokens. (In at least some embodiments, the recipient is tasked to detect the odd token—this is discussed in greater detail below.) By way of example, and not by way of limitation, one token can be "v" (the test token, also referred to herein as the stimulus sound) and another token can be "s" (the reference token, also referred to herein as the background sound), and the hearing percept can be /v/ /v/ /v/ /v/ /s/ /v/ /v/ . . . . Also, it is noted that other percepts can be used, such as /v/ /v/ /s/. That is, a three button forced choice paradigm can be used instead of the more numerous paradigm just detailed. Any paradigm or discrimination setup that enables the teachings detailed herein and/or variations thereof can be used in at least some embodiments.

Figure 5A:
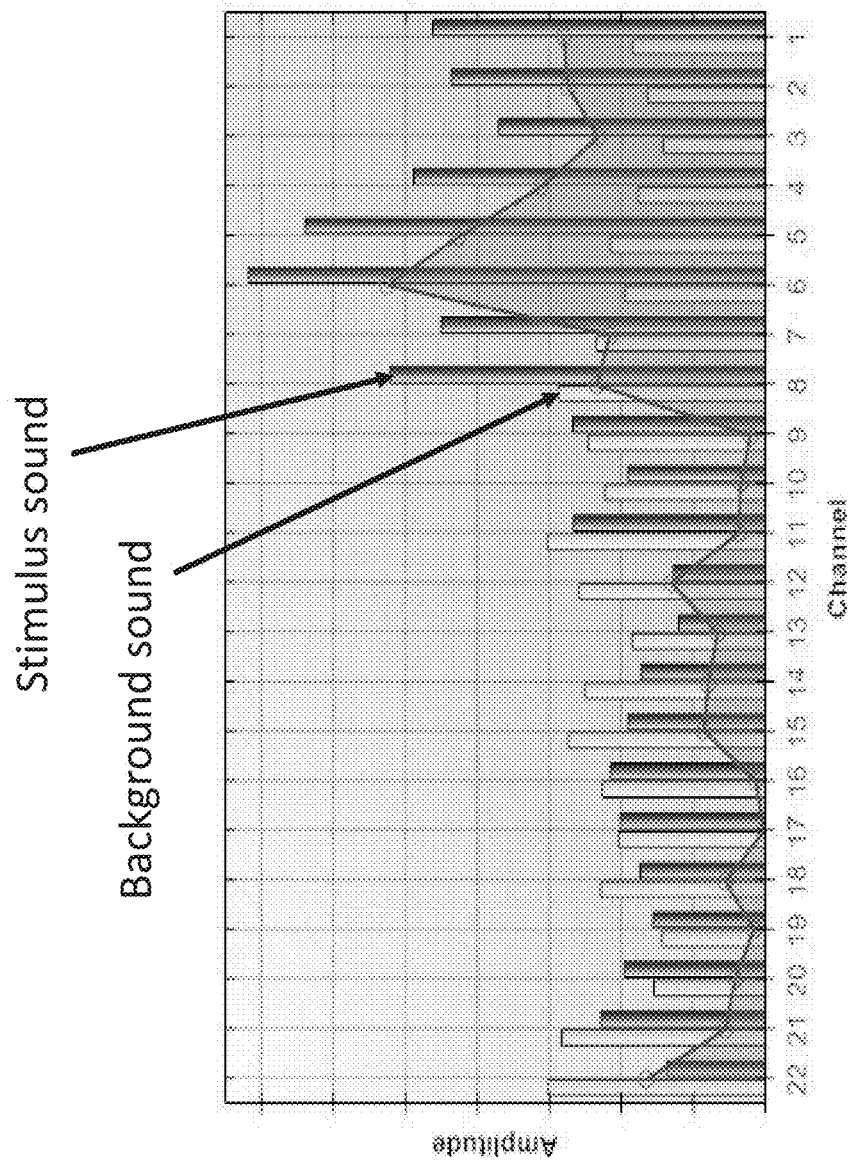
FIG. 5A presents a chart of exemplary data used to explain an exemplary embodiment.

FIG. 5A provides exemplary spectral results for this hearing percept having this token sequence for each of the 22 channels of the cochlear implant. The solid line corresponds to the absolute value difference between the amplitude (signal strength) of the two tokens (token pairs). It is noted that the chart of FIG. 5A can be developed utilizing the aforementioned token pairs utilizing the odd man out method or any other method that can enable the spectral content for a given tokens to be achieved that can enable the teachings detailed herein and are variations thereof to be practiced.

Figure 5B:
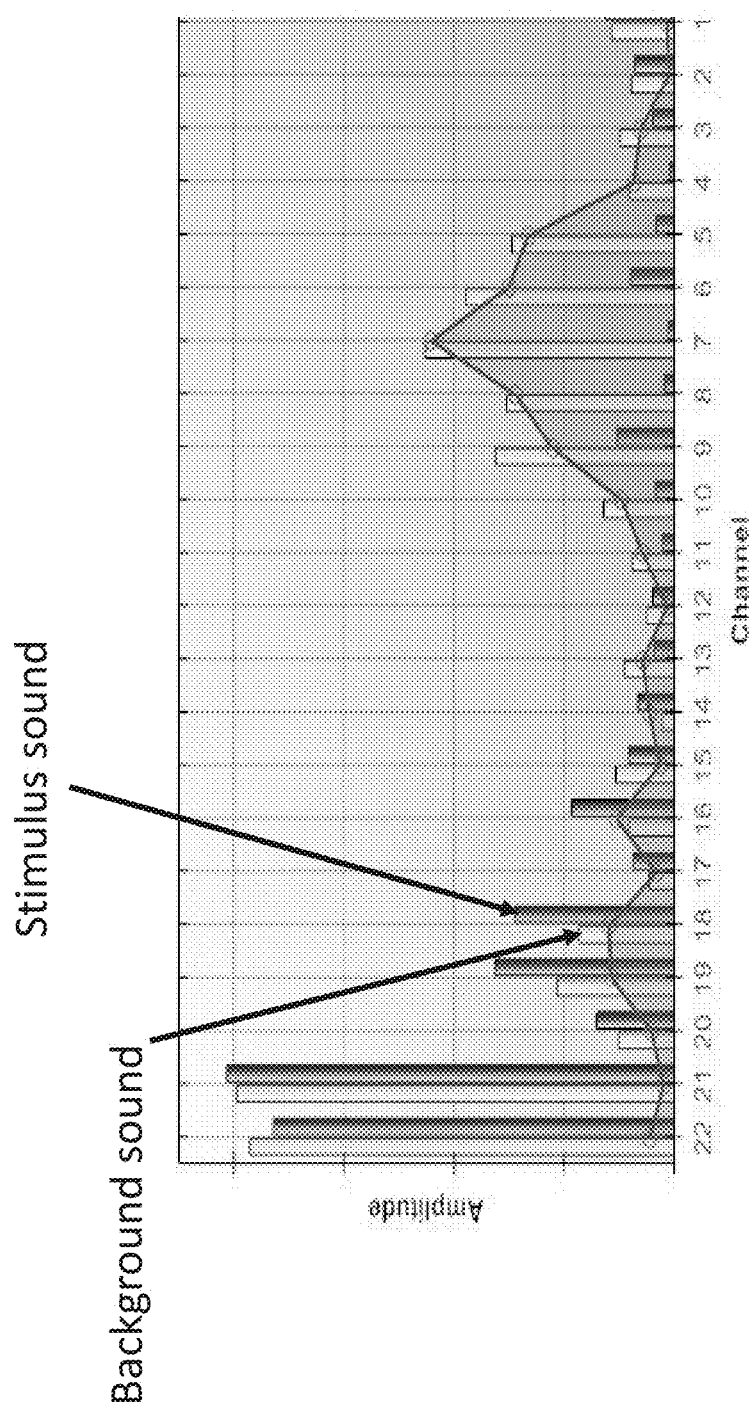
FIG. 5B presents a chart of exemplary data used to explain an exemplary embodiment.

Briefly, FIG. 5B provides another chart depicting exemplary spectral results for a hearing percept for a different token having a token sequence /i/ /i/ /i/ /i/ /i/ /u/ /i/ /i/ /i/ . . . .

As noted above, empirical methods can be utilized to execute method action 420. That said, in an alternative embodiment, method action 420 can be executed by obtaining the frequency based data for the respective tokens without actually executing the aforementioned test. Instead, it can be enough to obtain results of the test executed by some other entity. Any method that can enable method action 420 to be practiced can be utilized in at least some embodiments.

The results of method action 420 can entail obtaining a dataset that can be put in the format of a vector for a given token, where each entry corresponds to a signal level of a given channel of the cochlear implant 100. While the charts of FIGS. 5A and 5B are presented in terms of a 22 channel cochlear implant, for the purposes of discussion herein, a 10 channel cochlear implant will be referenced for ease of discussion (e.g., presenting a 10 entry vector is less cumbersome than presenting a 22 entry vector, presenting a 4×10 matrix or a 6×10 matrix is less cumbersome than presenting a 4×22 or 6×22 matrix, etc.). It is noted that the principals detailed herein with respect to the 10 channel cochlear implant are applicable to any type of cochlear implant having multichannel capabilities, including the 22 channel cochlear implant.

An exemplary result of method action 420 is a dataset that contains ten signal strength values. An exemplary embodiment entails placing these values into a 10 value vector for ten channels for the token "a," as seen by way of example only and not by way of limitation in the below vector.

[16.413  49.334  41.0701  51.9477  51.4024  51.8822  54.0889  52.8296  37.9022  15.6698]

The above values represent the signal strength value (in dBSPL) for respective frequency bands, with 16.413 corresponding to the signal level for channel 1 for the hearing percept, and 15.6698 corresponding to the signal level for channel 10, channel 1 being the band having the lowest frequencies, and channel 10 being the band having the highest frequencies. (It is noted that in embodiments where the number of channels of the cochlear implant 100 is 22, the vector would have 22 entries.)

Below are exemplary results for method action 420 for tokens "i," "o" and "u," respectively (having the channel sequence concomitant with that for the vector for "a").

[20.9335  55.5734  32.4698  21.0538  14.1629  21.9134  47.0046  45.3101  33.6032  18.1135]
[18.9897  59.0555  38.6913  45.638   27.3523  18.5764  30.151   34.8364  12.1682  13.3675]
[20.2756  58.7004  34.8571  25.5902  12.7624  10.5599  30.6435  18.31     9.9376  18.2829]

It is noted that the above three vectors and the vector above that can be combined into a 4×10 matrix. Any way of presenting or otherwise marshalling the data can be utilized in at least some embodiments of method action 420.

Figure 6:
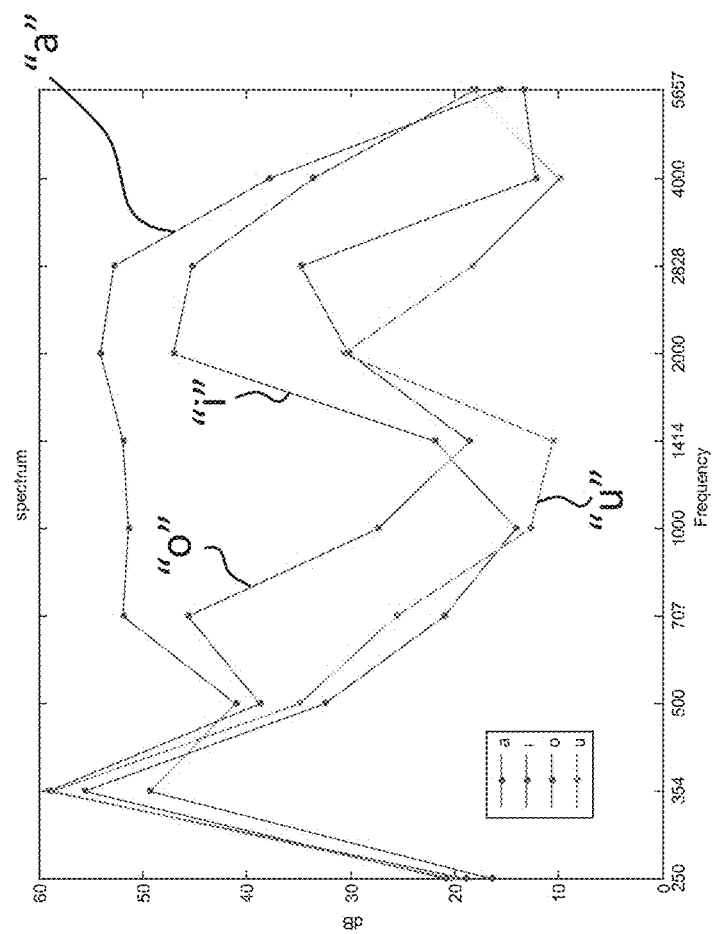
FIG. 6 presents a graph of exemplary data used to explain an exemplary embodiment.

FIG. 6 presents an exemplary graph depicting the spectrum for each of the four tokens over the ten frequency bands. From the above vectors and/or from FIG. 6, it can be clearly seen that the token "a" has the most energy in the mid and high frequencies. In contrast, the tokens "u," and "o" do not have most of their energy in the high frequencies (the tokens do not have, relatively speaking, a lot of energy in the high frequencies).

In view of the above, but now with reference to method 460 of FIG. 4B, it is noted that at least some of the sub-actions entailing the action of obtaining the frequency based data obtained in method action 420 can correspond to executing method action 465, which entails obtaining data indicative of an ability of a recipient of a hearing prosthesis to discriminate between tokens of respective token pairs of a plurality of token pairs in respective evoked hearing percepts induced by the hearing prosthesis. Concomitant with the above exemplary embodiment of method action 420, the obtained data obtained in method action 465 is based on empirical results that differentiate token pairs having tokens correctly discriminated by the recipient from token pairs having tokens conflated by the recipient, and the obtained data is based on respective signal strength data for respective frequency bands for specific tokens of the token pairs of the plurality of token pairs.

With reference back to FIG. 4A, method 400 further includes method action 430, which entails manipulating the frequency based data obtained in method action 420 based on an ability of the recipient to correctly distinguish between tokens of the respective tokens. In an exemplary embodiment, as noted above, token pairs are presented to the recipient utilizing an odd man out method to determine or otherwise estimate the ability of the recipient to correctly distinguish between tokens. For example, with reference to the tokens "a," "i," "o," and "u," token pairs a-i, a-o, a-u, i-o, i-u and o-u are presented to the recipient (six (6) token pairs) by evoking pertinent hearing percepts with the hearing prosthesis. Accordingly, in an exemplary embodiment, the obtained frequency based data for respective tokens is for a plurality of token pairs of the six tokens.

It is noted that the maximum number of pairs will be, in some embodiments, $n(n-1)/2$ when every token is paired with every other token. That said, it is noted that in at least some embodiments, not every pair will be utilized. A subset of the total number of pairs, such as with the more confusing pairs, can be utilized.

An exemplary embodiment entails obtaining a spectral difference matrix $\Delta S$ by obtaining the absolute value of the difference between the spectra for respective frequency bands of each pair. Accordingly, an exemplary embodiment of the manipulation action of action 430 entails obtaining respective absolute value signal strength based data for the token pairs. For example, the absolute value for the difference for the token pair a-i would be the following vector:

[4.5205  6.2393  8.6003  30.8938  37.2394  29.9687  7.0843  7.5195  4.299  2.4437]

The above vector is obtained by subtracting the vector for the token "a" from the vector for the token "i." It is noted that it is not necessary to place the data into vectors. Any form of data manipulation that can enable the teachings detailed herein and/or variations thereof to be practiced can be utilized in at least some embodiments. By way of example only and not by way of limitation, the data can be manipulated by subtracting the signal strength value for the first frequency band for the token "a" from the signal strength value for the first frequency band for the token "i," and so on for each of the bands (while also obtaining the absolute value difference for each band).

The absolute value for the difference for the token pair a-o would be the following vector:

[2.5767  9.7214  2.3788  6.3096  24.05  33.3057  23.938  17.9932  25.734  2.3023]

The absolute value for the difference for the token pair a-u would be the following vector:

[3.8626  9.3664  6.2129  26.3574  38.6399  41.3223  23.4455  34.5196  27.9646  2.6131]

The absolute value for the difference for the token pair i-o would be the following vector:

[1.9438  3.4821  6.2215  24.5842  13.1894  3.337  16.8537  10.4737  21.435  4.746]

The absolute value for the difference for the token pair i-u would be the following vector:

[0.6578  3.127  2.3873  4.5364  1.4005  11.3535  16.3612  27.0001  23.6656  0.1694]

The absolute value for the difference for the token pair o-u would be the following vector:

| | | | | | | | | | |
|---|---|---|---|---|---|---|---|---|---|
| [1.2859 | 0.3551 | 3.8341 | 20.0478 | 14.5899 | 8.0165 | 0.4925 | 16.5264 | 2.2306 | 4.91] |

Figure 7:
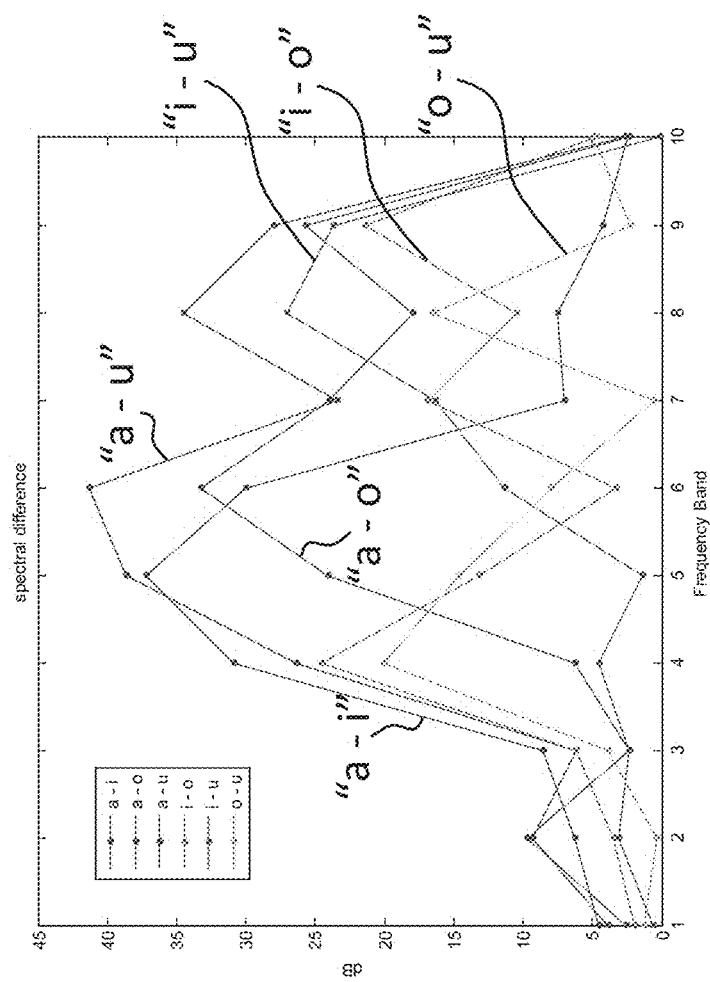
FIG. 7 presents a graph of exemplary data used to explain an exemplary embodiment.

The above vectors represent the difference between the spectral energies for the channels for each of the token pairs (absolute value difference). Graphically, the above vectors are presented in FIG. 7.

As noted above, method action 430 can be executed by placing the data into matrices and utilizing matrix manipulation techniques. For example, a 4×10 matrix S could be constructed based on the vectors for the individual tokens as follows:

| | | | | | | | | | |
|---|---|---|---|---|---|---|---|---|---|
| 16.413 | 49.334 | 41.0701 | 51.9477 | 51.4024 | 51.8822 | 54.0889 | 52.8296 | 37.9022 | 15.6698 |
| 20.9335 | 55.5734 | 32.4698 | 21.0538 | 14.1629 | 21.9134 | 47.0046 | 45.3101 | 33.6032 | 18.1135 |
| 18.9897 | 59.0555 | 38.6913 | 45.638 | 27.3523 | 18.5764 | 30.151 | 34.8364 | 12.1682 | 13.3675 |
| 20.2756 | 58.7004 | 34.8571 | 25.5902 | 12.7624 | 10.5599 | 30.6435 | 18.31 | 9.9376 | 18.2829 |

Every column of the above vectors is the spectrum in dBSPL of a given token, and the matrix can be represented by: $S(k,f)$, where k represents the token and f represents the frequency band. It is noted that for a cochlear implant 100 having 22 channels, the above matrix would be a 4×22 matrix (and if 14 tokens were used, a 14×22 matrix).

Further, the absolute value differences can be represented as a spectral difference matrix $\Delta S$ as follows:

| | | | | | | | | | |
|---|---|---|---|---|---|---|---|---|---|
| 4.5205 | 6.2393 | 8.6003 | 30.8938 | 37.2394 | 29.9687 | 7.0843 | 7.5195 | 4.299 | 2.4437 |
| 2.5767 | 9.7214 | 2.3788 | 6.3096 | 24.05 | 33.3057 | 23.938 | 17.9932 | 25.734 | 2.3023 |
| 3.8626 | 9.3664 | 6.2129 | 26.3574 | 38.6399 | 41.3223 | 23.4455 | 34.5196 | 27.9646 | 2.6131 |
| 1.9438 | 3.4821 | 6.2215 | 24.5842 | 13.1894 | 3.337 | 16.8537 | 10.4737 | 21.435 | 4.746 |
| 0.6578 | 3.127 | 2.3873 | 4.5364 | 1.4005 | 11.3535 | 16.3612 | 27.0001 | 23.6656 | 0.1694 |
| 1.2859 | 0.3551 | 3.8341 | 20.0478 | 14.5899 | 8.0165 | 0.4925 | 16.5264 | 2.2306 | 4.9100 |

The matrix can be represented by: $\Delta S(k,f)=|S(i,f)-S(j,f)|$ for a token pair k equal to $\{i, j\}$. As seen above, this results in a 6×10 matrix (and would result in a 6×22 matrix for a cochlear implant with 22 channels, and a 20×22 matrix for such a cochlear implant where 20 tokens where 14 tokens were utilized (20 token pairs)).

The actions detailed above to develop the $\Delta S$ matrix are examples of obtaining respective signal strength differences between respective signal strength data for the two first tokens, thereby obtaining the respective signal strength data for the one or more first token pairs, where the $\Delta S$ matrix and the data used to support that matrix correspond to the aforementioned signal strength data. From the absolute value vectors (or $\Delta S$ matrix), it can be seen that some token contrasts contain more energy than others. For example, the token pair a-u has more energy than the token pair o-u for 9 out of the 10 frequency bands, and more energy for the mean and median and the total of the frequency bands. That said, there is utilitarian value in normalizing the spectral differences. In an exemplary embodiment, this can be achieved by dividing the spectral differences by the total spectral difference (summed across the bands—effectively obtaining a percentage value of the total spectral difference). It is noted that there is also utilitarian value in applying a power coefficient to smooth or amplify any spectral differences. By way of example, a power coefficient of 2 is applied to the above $\Delta S$ matrix, and the resulting spectral differences are divided by the total spectral difference. The resulting matrix is presented below (hereinafter referred to as the weighted matrix):

| | | | | | | | | | |
|---|---|---|---|---|---|---|---|---|---|
| 0.5832 | 1.111 | 2.111 | 27.2395 | 39.5787 | 25.6326 | 1.4323 | 1.6137 | 0.5275 | 0.1704 |
| 0.1954 | 2.7807 | 0.1665 | 1.1714 | 17.0188 | 32.639 | 16.8606 | 9.5261 | 19.4856 | 0.156 |
| 0.2272 | 1.336 | 0.5878 | 10.5794 | 22.7367 | 26.003 | 8.3709 | 18.1462 | 11.9089 | 0.104 |
| 0.2197 | 0.705 | 2.2506 | 35.1423 | 10.115 | 0.6475 | 16.5161 | 6.3785 | 26.7156 | 1.3097 |
| 0.0251 | 0.5671 | 0.3306 | 1.1936 | 0.1138 | 7.4764 | 15.5259 | 42.2824 | 32.4835 | 0.0017 |
| 0.1657 | 0.0126 | 1.473 | 40.2709 | 21.3286 | 6.4392 | 0.0243 | 27.3663 | 0.4985 | 2.42 |

The values indicate how important a given frequency band is, relative to other frequency bands, for a given token pair having a spectral contrast. Accordingly, the obtained frequency based data for respective tokens is for a plurality of token pairs of the tokens, and the action of manipulating the frequency based data entails mathematically manipulating the frequency based data to identify frequency bands that are relatively more important relative to other frequency bands for token pairs having tokens that were not correctly discriminated when the hearing percepts were evoked. Still further, in an exemplary embodiment, manipulating the frequency based data entails mathematically manipulating the frequency based data to identify frequency bands that are relatively more important relative to other frequency bands for token pairs having tokens that were not correctly discriminated when the hearing percepts were evoked while discounting for token pairs having tokens that were correctly discriminated.

The ΔS matrix and/or the underlying vectors used to establish the ΔS matrix constitutes respective signal strength data for respective frequency bands for one or more token pairs that is based on two or more token pairs. In the example above, at least one of the token pairs represents tokens conflated by the recipient, and at least one other of the token pairs represents tokens correctly differentiated by the recipient (in the example below utilizing the above data, there are two token pairs that represent tokens conflated by the recipient, and for token pairs that represent tokens that were correctly discriminated by the recipient). There can be any number of token pairs representing tokens correctly differentiated or conflated (out of the entire number of token pairs).

The above weighted matrix can be obtained by the equation:

$$W(k,f) = \Delta S(k,f)^p / \Sigma_i \Delta S(k,i)^p$$

where, p is a positive power coefficient.

The more important coefficients approach 100 when summed over all frequencies (bands). For p=1, the band importance is the normalized spectral difference. Thus, in some embodiments, the obtained data obtained in method action 465 is data indicative of a relative importance of frequency bands for at least one token pair of a plurality of token pairs (e.g., such as the token pair with conflated tokens/with tokens that were not correctly discriminated), and, in some embodiments, it is indicative of a relative importance of frequency bands for all token pairs of the plurality of token pairs.

Figure 8:
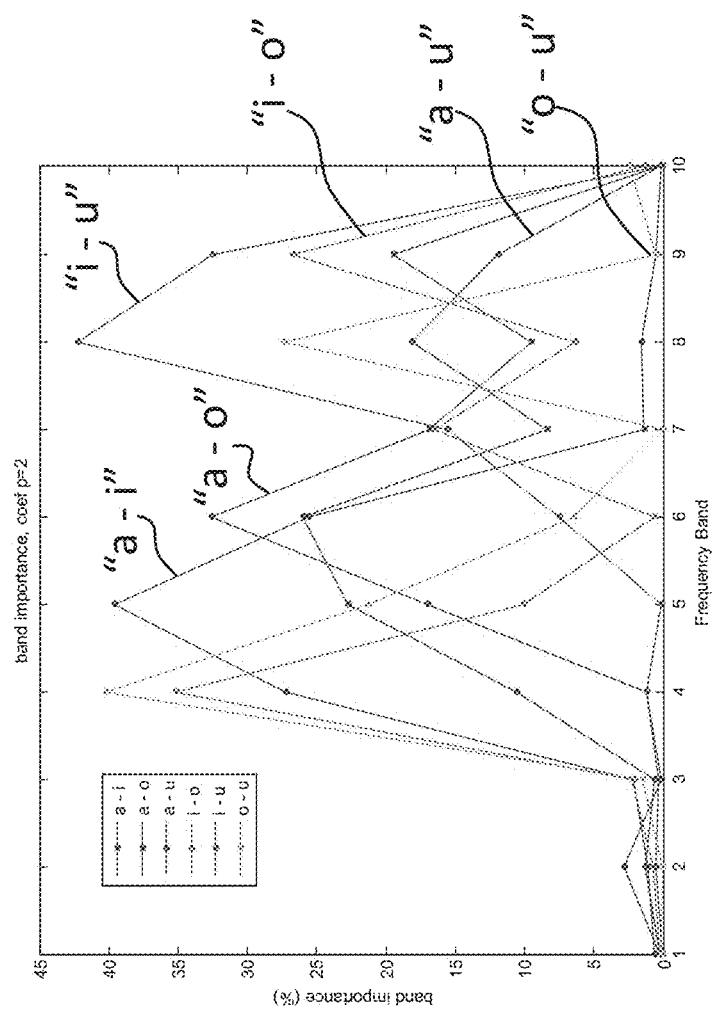
FIG. 8 presents a graph of exemplary data used to explain an exemplary embodiment.

FIG. 8 presents a graph of the data of the above weighted matrix where p=2.

In view of the above, it can be seen that the weighted matrix and/or the ΔS matrix can be utilized to estimate or otherwise ascertain the importance (or more accurately, relative importance) of a given frequency band for a given token pair presented in the discrimination test. It is further noted that the weighted matrix and/or the ΔS matrix can be developed without regard to whether the recipient correctly discriminated and/or conflated tokens of a given token pair.

The weighted matrix (or the collective vectors) can be further manipulated into a single dataset, such as a vector, based on whether or not the recipient correctly discriminated (which includes whether the recipient conflated) the tokens of the token pairs (e.g., the stimulus sound from the background sound). In an exemplary embodiment, this entails grouping the datasets for each token pair (e.g., the respective vectors) into two groups: a first group corresponding to the token pair(s) including tokens that were not correctly discriminated/were conflated, and a second group corresponding to the token pair(s) including tokens that were correctly discriminated/were not conflated. Still further in this exemplary embodiment, the vectors of the first group are added together (or the data is manipulated in some manner to create a value indicative of the collective for the first groups—any manipulation that will enable the teachings detailed herein and are variations thereof to be practiced) and the vectors of the second group are added together (or manipulated in some other manner), and the resulting latter vector is subtracted from the resulting former vector (or some other manipulation is performed between the two groups to ascertain data indicative of the difference between the two). Put another way, the components of the vector(s) of the first group are assigned positive values, the components of the vector(s) of the second group are assigned negative values, and all the vectors are added. The resulting vector is hereinafter referred to as the relative contribution vector, because it presents the relative contribution of given token pairs that were not discriminated/were conflated because the higher the value of the component of the vector, the more that the corresponding band contributed to the non-discriminated token pair. Any device, system and/or method that can enable the relative contribution of token pairs that were not discriminated/were conflated can utilize in at least some embodiments.

By way of example only and not by way of limitation, in a scenario where the cochlear implant recipient failed to correctly discriminate the tokens of token pair a-i and the tokens of token pair o-u, the resulting relative contribution vector is as follows:

[0.0815  −4.2652  0.2485  19.4237  10.923  −34.694  −55.816  −47.353  −89.567  1.019]

The above vector can be obtained utilizing the following exemplary equation, where "c" is the coefficient vector $$c(f) = (\Sigma_{wrong} w(i,f) - \Sigma_{correct} w(i,f)),$$

where the coefficient c for a given frequency band entails the summation of the importance contributions of the wrong pairs minus the importance contributions of the correct pairs. In an exemplary embodiment, channels with a relatively large positive coefficient are changed, whereas the electrodes having relatively large negative coefficients are not changed. Channels with a relatively small positive coefficient may or may not be changed, depending on circumstances that could vary from recipient to recipient and/or with respect to economic circumstances (whether there are diminishing returns for spending additional time to address these channels as opposed to spending the time in other fitting/quality control actions).

Figure 9:
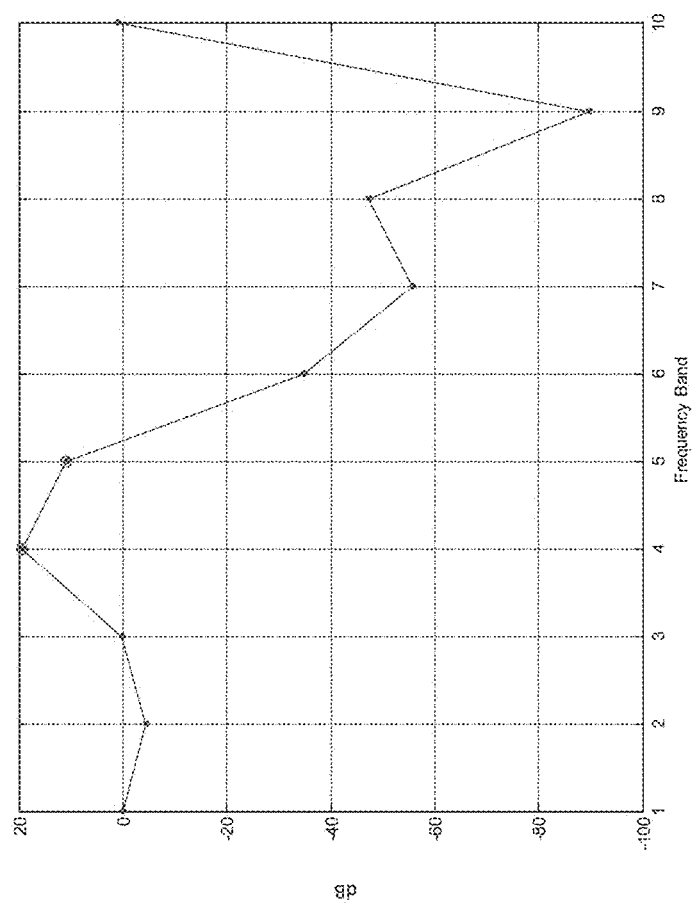
FIG. 9 presents a graph of exemplary data used to explain an exemplary embodiment.

This relative contribution vector is plotted in FIG. 9. Again, there are other ways to present the resulting relative contribution data (i.e., the data need not be in vector form).

Accordingly, an exemplary embodiment of manipulating the frequency based data entails merging the respective absolute value signal strength based data (which includes normalized data, because it is based on the signal strength) for the token pairs. More specifically, the action of merging the signal strength based data for the token pairs entails obtaining a discrete set of frequency band specific data by summing or otherwise obtaining a collective indicative of the absolute value signal strength based data for token pairs having tokens conflated (not discriminated) by the recipient and discounting that summation by the absolute value signal strength based data for token pairs having tokens correctly discriminated by the recipient.

As can be seen from the above relative contribution vector, channels 4 and 5 correspond to the frequency bands that most contributed to the pairs that were not discriminated, at least when the vectors of the first group are discounted for the contribution made by frequency bands for the tokens that were correctly discriminated. Accordingly, based on the manipulation of the data in method action 430, channels 4 and 5 are the channels with respect to the map that are to be adjusted.

It is noted that the above example provides a quite clear difference between the values of channels four and five and the other values. An exemplary algorithm can entail normalizing the vector by summing the absolute values of the values of the relative contribution vector, and dividing the individual values by the sum and multiplying by 100. That is, converting the vector into a percentage of the sum. Such a vector is as follows (hereinafter referred to as the normalized relative contribution vector):

[0.030942 −1.6193 0.094346 7.3744 4.1470 −13.172 −21.191 −17.978 −34.005 0.38687]

Utilizing the normalized relative contribution vector, or even the non-normalized relative contribution vector, it is possible to identify one or more frequency bands of the plurality of frequency bands for one or more first token pairs where the respective signal strength data indicates relatively higher signal strength relative to that of one or more other frequency bands for the one or more token pairs (and an exemplary embodiment includes a method including the action of identifying one or more frequency bands of the plurality of frequency bands for the one or more first token pairs where the respective signal strength data indicates relatively higher signal strength relative to that of one or more other frequency bands for the one or more token pairs). That said, it is possible to accomplish the aforementioned identification using, for example, the ΔS matrix, or the underlying data used to develop the ΔS matrix (e.g., the absolute values for the difference for the various token pairs, in vector form or otherwise). Any method or dataset that can enable the identifying one or more frequency bands of the plurality of frequency bands for the one or more first token pairs where the respective signal strength data indicates relatively higher signal strength relative to that of one or more other frequency bands for the one or more token pairs can be utilized in at least some embodiments, providing that the teachings detailed herein are enabled.

Accordingly, in view of the above, utilizing the relative contribution vector (normalized or otherwise), the electrodes for which it may be utilitarian to change or otherwise adjust the map parameters thereof can be identified. That is, these vectors can be utilized to determine the set of electrodes to be modified (where a set can include one or more electrodes).

Assigning a threshold of, for example, 3%, where any frequency band having a positive value above 3% of the average of the absolute values in the vector is a candidate for adjustment, only channels 4 and 5 are adjusted. Indeed, a threshold of 1% results in only channels 4 and 5 being adjusted. Conversely, a threshold value of 5% results in only channel 4 being adjusted, and a threshold of 10% results in no channel being adjusted. The threshold can be set based on any value deemed utilitarian. Any other benchmark can be used to determine what bands are important other than the percentage above the absolute values).

Figure 10:
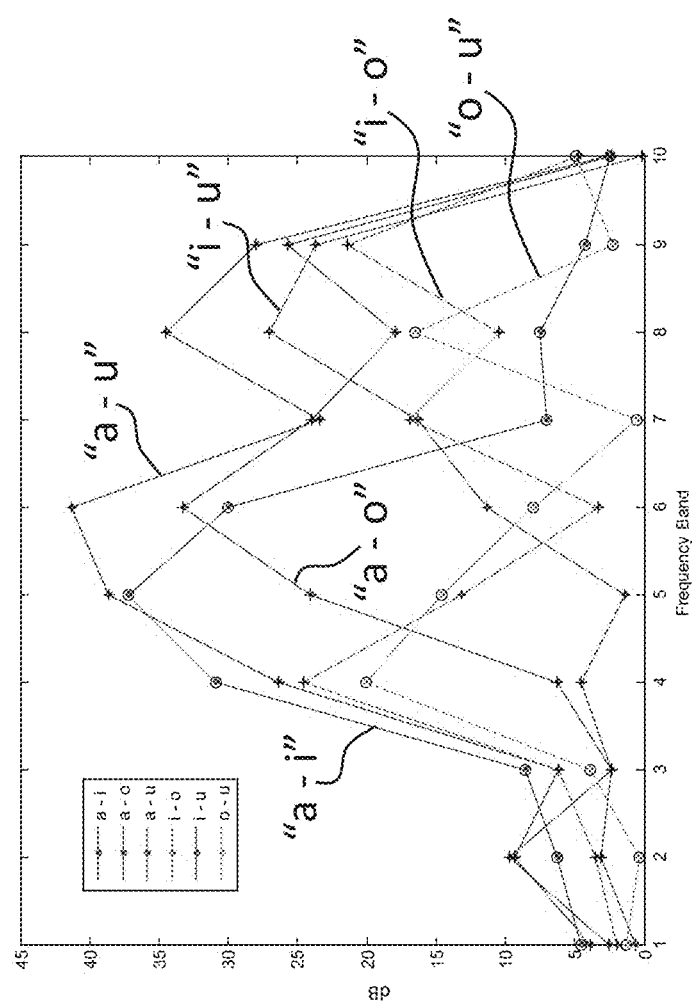
FIG. 10 presents a graph of exemplary data used to explain an exemplary embodiment.

The above said, in some alternate embodiments of executing method action 430, a relative contribution vector is not developed. Instead, the data of the obtained spectral difference matrix ΔS obtained by taking the absolute value of the difference between the spectra for respective frequency bands of each pairs can be plotted, with an indication of the pairs that were correctly discriminated and/or not correctly discriminated. This is seen in FIG. 10, with the curves for the pairs correctly discriminated provided with "+" symbols for the specific data points, and the curves for the pairs incorrectly discriminated provided with "o" symbols for the specific data points. A visual inspection of the data of FIG. 10 reveals that frequency bands 4 and 5 have relatively high spectral contrast values for token pairs that were not discriminated, with relatively low spectral contrast values for token pairs that were discriminated.

In view of the above, it can be seen that some exemplary embodiments are such that the action of obtaining respective first signal strength data entails a step for performing a function of creating a matrix having columns corresponding to the respective first frequency bands and rows corresponding to respective first tokens, the values of the matrix corresponding to the respective first signal strength data. Further, the action of obtaining respective spectral energy differences entail a step for performing a function of creating a matrix based on absolute value differences between values of respective columns of the matrix for respective token pairs, and a step for performing a function of creating a vector having columns corresponding to the respective first frequency bands by subtracting rows of the obtained matrix corresponding to token pairs representing tokens correctly differentiated by the recipient from a sum of the rows of the obtained matrix corresponding to token pairs resenting tokens conflated by the recipient.

It is noted that while the above teachings are directed towards identifying token pairs having tokens that were not correctly discriminated/identifying token pairs having tokens that were conflated, in at least some instances, some token pairs will be correctly discriminated sometimes, while in other instances that same token pair will not be correctly discriminated. Accordingly, the above teachings can take into account the percentage of time that the given token pair is correctly discriminated/conflated. This can be used to weight any of the data above. Alternatively and/or in addition to this, this can be used to determine a threshold as to whether or not to determine that a given token pair was correctly discriminated. For example, if a token pair was correctly discriminated in 6 out of 10 presentations, it may be considered that that token pair was correctly discriminated for the purposes of the data manipulation detailed above. Alternatively, by way of example only and not by way of limitation, it may be considered that that token pair was not correctly discriminated, but the spectral difference calculations are discounted by a certain percentage (e.g., 40%).

Referring back to FIG. 4, method 400 includes method action 440, which entails adjusting an output control of the hearing prosthesis with respect to one or more frequency bands of a plurality of frequency bands of the hearing prosthesis based on the data manipulated in method action 430. This can correspond to adjusting parameters of the hearing prosthesis based on identified frequency bands. For example, based on the manipulated data, with respect to the just-described example having a threshold value of 3%, channels 4 and 5 would be adjusted, where channels 4 and 5 correspond to the identified frequency bands. Method action 440 can be executed by changing the electrical map parameter for a particular channel of the cochlear implant. In an exemplary embodiment, this can entail changing the C-level of the map for that given channel. In an exemplary embodiment, at least in some instances, an upward adjustment on the C-level in a given channel will be made. In an exemplary embodiment, a 2% increase in the C-level is implemented for a given channel. In an alternative exemplary embodiment, a 3% increase in the C-level is implemented for a given channel. In an alternative exemplary embodiment, a 4% increase in the C-level is implemented for a given channel. In an alternative exemplary embodiment, a 5% increase in the C-level is implemented for a given channel. In an alternative exemplary embodiment, a 6% increase in the C-level is implemented for a given channel. In an alternative exemplary embodiment, a 7% increase in the C-level is implemented for a given channel. In some embodiments, the increase is about 1% to about 15% or any value or range of values therebetween in 0.01% increments (e.g., about 3.06%, about 7.19%, about 4.33% to about 13.43%, etc.). It is also noted that the percentage change in the adjustments can be variable, depending on circumstances.

Figure 11:
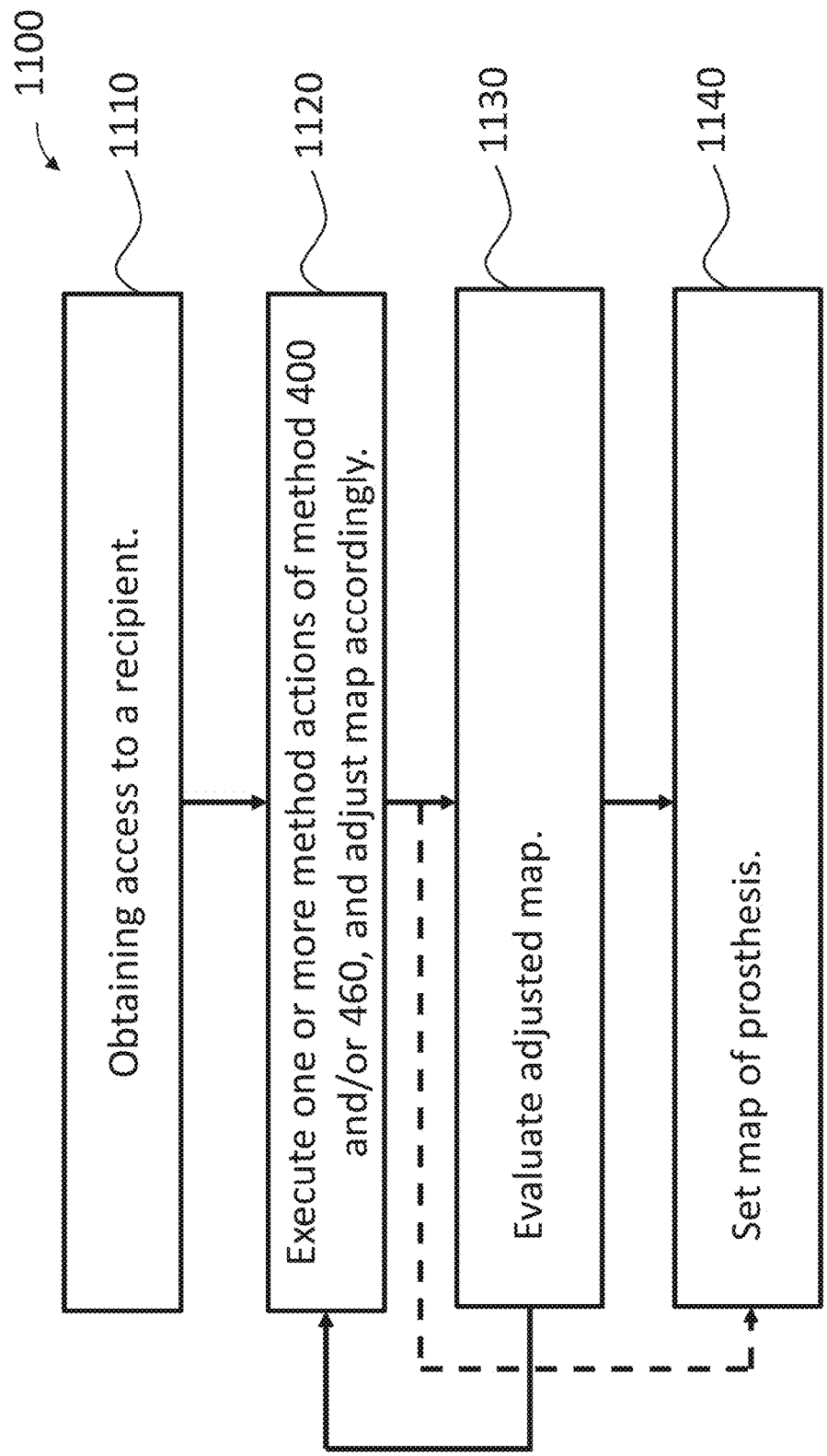
FIG. 11 presents another exemplary flowchart according to an exemplary embodiment.

After the adjustments are made to the given channels, the map can be set based on those adjustments and the cochlear implants 100 can be programmed with that map. The recipient of the hearing prosthesis will then go on to utilize the cochlear implant in normal use based on that map, adjusted according to the teachings detailed herein. That said, in an alternate embodiment, after adjusting the map, some or all of the teachings detailed herein and/or variations thereof can be repeated as a quality check of the like one in the adjusted map. If it is determined that there are a number of token pairs that still resist proper discrimination by the recipient and/or that the map can be further adjusted in an economical manner, the channels can be further adjusted, the map is then set (or another quality check is performed, etc.), and the recipient uses the cochlear implant 100. FIG. 11 presents an exemplary flowchart for this concept. More specifically, FIG. 11 presents method 1100, which includes method action 1110, which entails obtaining access to a recipient having a cochlear implant and/or other hearing prosthesis. Method action 1110 can be executed in accordance with any of the method actions detailed above and/or variations thereof. Method 1100 further includes method action 1120, which entails executing one or more of the method actions of method 400 and/or method 460 (or another method action detailed herein), and adjusting the map of the cochlear implant or other hearing prosthesis accordingly. Method action 1130 entails evaluating the adjusted map adjusted in method action 1120. This can be done by performing any of the actions detailed herein, such as by way of example only and not by way of limitation, executing the empirical discrimination test detailed above and/or obtaining data based on one another discrimination test that was executed by another entity after method action 1120 was executed. Based on the evaluation of the adjusted map, the method returns back to method action 1120 or method action 1110 if method action 1130 was executed without access to the recipient, and method action 1120 is repeated (albeit potentially using different method actions), and the adjusted map is optionally reevaluated. Method 1100 further includes method action 1140, which entails setting the map of the prosthesis, and sending the recipient off to utilize the prosthesis in a normal manner. It is noted that in at least some embodiments, method action 1130 might be skipped. That is, after one or more of the method actions of method 400 and/or method 460 are executed, and the map is adjusted accordingly, there is no evaluation of the adjusted map.

It is further noted that while the various methods detailed herein are presented in a given order, in alternative embodiments, the order can be adjusted providing that the teachings detailed herein are enabled.

It is noted that at least some embodiments, there is the additional action of determining how and/or how much to change the electrical map parameters for a particular electrode in order to improve discrimination capability, or at least based on the manipulated data. As noted above, in at least some embodiments, the comfort level is the map parameter that is adjusted. That said, in alternative embodiments, the threshold level instead or in addition to this can be adjusted. Alternatively and/or in addition to this, other map parameters can be adjusted, such as by way of example only and not by way of limitation, gain, Q, T-SPL, etc.). Any map parameter that can be adjusted that would be considered to result in an increase in the likelihood that the recipient will be able to better discriminate between tokens of token pairs previously incorrectly discriminated can be adjusted in at least some embodiments.

It is noted that some exemplary embodiments of method action 440 entail utilizing the manipulated data to determine if an electrode is contributing to various wrong token pairs. Alternatively and/or in addition to this, some exemplary embodiments of method action 400 further entail utilizing the manipulated data to determine if an electrode is contributing to correct pairs (in which case the electrode would not be adjusted). Thus, at least some embodiments entail utilizing both a quantitative and a qualitative approach in evaluating the manipulated data.

Indeed, it is noted that in at least some embodiments, the increase in the C-level that is implemented for a given channel is based on the difference between the values of the relative contribution vector (normalized or otherwise), or other dataset(s) where, in an exemplary embodiment, the greater the differences between various frequency bands, the greater the increase, and the lower the differences, the lower the increase.

Accordingly, in an exemplary embodiment of method action 440, the action of adjusting an output of the hearing prosthesis in one or more frequency bands of a plurality of frequency bands entails adjusting output controls in only some of the frequency bands of the plurality of frequency bands of the hearing prosthesis. For example, only channels 4 and 5 are adjusted. The map for the other channels is not adjusted (at least for the 3% threshold). Thus, the aforementioned example is an example where frequency channel(s) that are adjusted are channels corresponding to frequency bands having respective token pair relative spectral energies (e.g., based on the values of the relative contribution vector or the normalized relative contribution vector) that are higher than other respective token pair relative spectral energies.

In view of the above, it is noted that executing at least some of the sub-actions that result in the execution of an exemplary embodiment of method action 440 results in method action 470 of method 460, which corresponds to adjusting one or more but less than all frequency channels of a plurality of frequency channels of the hearing prosthesis based on the data obtained in method action 420. In an exemplary embodiment, method action 470 entails adjusting the channels of the cochlear implant 100 corresponding to those having relatively higher relative importance (relative to the other channels) with respect to at least one of the token pairs (e.g., the ones having the tokens that were conflated).

Accordingly, the result of method action 450 and/or 470 can entail adjusting one or more frequency channels such that an output energy of the hearing prosthesis at the adjusted one or more frequency channels, relative to that which was the case when the hearing percepts were evoked (e.g., to obtain the empirical data detailed above), is higher (i.e., increasing the relative output energy). This can be done by increasing the current level of the given channel. Indeed, in an exemplary embodiment of method action 450 or 470, the action entails increasing a relative current level of one or more channels of the hearing prosthesis corresponding to an identified one or more frequency bands, a percentage increase of the increase being greater than a percentage increase of any increase (which may be zero in the scenario of no increase) of the non-identified frequency bands.

As detailed above, at least some of the teachings detailed herein and/or variations thereof enable an audiologist or clinician or other professional to improve a given map for a hearing prosthesis, or at least obtain indication that the map that results from at least a partial fitting method is adequate and/or utilitarian (potentially as utilitarian as possible). In an exemplary embodiment, this can enable an audiologist, such as by way of example, a cochlear implant audiologist, to obtain a setting for at least comfort levels that improves upon that which is set for the given map, or at least obtaining an indication that the comfort levels such that map are adequate and/or utilitarian.

In at least some exemplary embodiments, the initial map (the map that is present prior to implementation of the teachings detailed herein—the map that results from the initial fitting/at least partial fitting process), is set in general, and the comfort levels are set in particular, by measuring the loudness of a pulse train provided by each electrode and/or a subset of each electrode. At the comfort level, the pulse train should, subjectively to the recipient, sound loud but not uncomfortable. Sounds of 65 to 70 dB will be mapped electrically to comfort level in at least some embodiments. Some exemplary fitting methods entail balancing the comfort levels on different electrodes to make sure that the recipient is making uniform loudness ratings across the electrode. In at least some instances of such, these ratings may be biased because many progressively deafening recipients will dislike the high-pitched quality of the basal electrodes and quickly state that they are too loud. In at least some exemplary embodiments, this exemplary scenario can be alleviated, at least in part, by practicing some and/or all of the teachings detailed herein and/or variations thereof.

As noted above, the frequency-based data can be obtained by providing the recipient with a test in which tokens are provided (e.g. token pairs). It is noted that the aforementioned test can be a discrimination test that is based on the detection of differences (i.e. discrimination) a stationary phonemes. It is noted that this test, when utilized in at least some embodiments of the teachings detailed herein, can be executed after the fitting process has begun, and after at least an embryonic map has been developed for the hearing prosthesis. In an exemplary embodiment, the aforementioned test is utilitarian value with respect to the teachings detailed herein by analyzing the phoneme pairs having tokens that were conflated with respect to their spectral contents, an exemplary result of that analysis being presented in FIGS. 5A and 5B.

At least some of the teachings detailed herein have utilitarian value with respect to addressing the negative effects that can result due to the fact that some electrodes are not effectively coupled to excitable neural tissue, threshold level and/or comfort levels are too soft, or one or more electrodes may mask one or more other electrodes, and/or IDR settings are too narrow. Accordingly, an exemplary embodiment entails executing some or all of the method actions detailed herein on a recipient where electrode is not effectively coupled to excitable neural tissue, threshold level and/or comfort levels are initially set to soft (i.e. in the initial/embryonic map resulting from the initial fitting process/the beginning of the fitting process) or one or more electrodes may mask one or more other electrodes and/or IDR settings are too narrow.

Indeed, an exemplary embodiment entails at least partially fitting a hearing prosthesis to obtain at least an embryonic map, and providing the aforementioned discrimination test. If the recipient passes the test (e.g., scores above a certain threshold such as being able to discriminate between tokens in 90% or more of the token pairs), the teachings herein are not implemented. Conversely, if the recipient does not pass the test, or otherwise the results of the test indicate that the map should be adapted in some manner, the teachings detailed herein are implemented.

It is noted that one or more or all of the methods detailed herein, in full or in part, can be, in at least some embodiments, practiced in the form of a non-transitory computer readable medium comprising a computer programming having code to execute one or more or all of the method actions detailed herein. Indeed, it is noted that any method detailed herein corresponds to a disclosure for a device and/or system configured to execute that method. Further, it is noted that any device and/or system detailed herein corresponds to a disclosure for a method corresponding to the functionality of that device and/or system (not only just a method of utilizing the device and/or system, but the method executed by that device and/or system).

Accordingly, in an exemplary embodiment, there is a non-transitory computer readable medium having recorded thereon, a computer program for executing at least a portion of a method of fitting an electrical stimulating device including electrodes implanted in a recipient (e.g., such as the cochlear implant 100 of FIG. 1). The electrical stimulating devices are configured to apply electrical stimulation to the recipient via the plurality of electrodes. In an exemplary embodiment, this computer program includes a code for executing method 400 and/or method 460.

It is noted that while the teachings detailed herein are described in terms of an electrical stimulating device in the form of a cochlear implant, it is noted that alternate embodiments are applicable to other types of stimulating devices. By way of example only and not by way of limitation, the teachings detailed herein and/or variations thereof can be applicable to a bone conduction device, a Direct Acoustic Cochlear Implant, or traditional hearing aids, at least those having channel features. Indeed, the embodiments where there is no specifically divided channels, proxy channels can be established. That is, the frequency spectrum can be divided into frequency bands for data manipulation purposes and the respective frequency bands can be treated as channel.

As noted above, at least some of the method actions can be executed at a location remote from where another method action is located. For example, is noted that an exemplary embodiment entails executing some or all of the method actions detailed herein where the recipient of the hearing prosthesis is located remotely (e.g., geographically distant) from where at least some of the method actions detailed herein are executed (e.g., any method action detailed herein that can be executed by, for example, a computer or other processor located at a remote location). For example, the method of flowchart 400 could be executed via internet communication with the hearing prosthesis and the user interface 314 and/or the hearing implant fitting system 306 (e.g., communication link 308 of FIG. 3 can be an internet connection or a wired or wireless connection). Still further by example, with respect to the method of flowchart 400, method action 410 can be executed at one location (controlled by the audiologist 304 at another location geographically remote from the one location), and method action 430 could be executed at the location where the audiologist 304 is located. That is, any method action herein can be executed at one location, and any method action herein can be executed at another location, and so on, providing that the teachings detailed herein and/or variations thereof can be practiced.

It is noted that any disclosure of a method action detailed herein corresponds to a disclosure of a corresponding system and/or device for executing that method action, in at least some embodiments, automatically. It is further noted that any disclosure of an apparatus or system herein corresponds to a disclosure of a method of operating that apparatus. It is also noted that any disclosure of any method action detailed herein further includes a disclosure of executing that method action in an automated fashion, as well as a device for executing those method actions in the automated manner.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
   obtaining data indicative of an ability of a recipient of a hearing prosthesis to discriminate between tokens of respective token pairs of a plurality of token pairs in respective evoked hearing percepts induced by the hearing prosthesis, wherein at least one of:
   (i) a first token pair of the plurality of token pairs is made up of different tokens relative to one another and a second token pair of the plurality of tokens is made up of different tokens relative to one another; or
   (ii) the first token pair of the plurality of token pairs and the second token pair of the plurality of token pairs collectively include at least three different tokens that are different tokens relative to one another; and
   adjusting one or more but less than all frequency channels of a plurality of frequency channels of the hearing prosthesis based on the obtained data.

2. The method of claim 1, wherein:
   the obtained data is based on empirical results that differentiate token pairs having tokens correctly discriminated by the recipient from token pairs having tokens conflated by the recipient.

3. The method of claim 1, wherein:
   the obtained data is data indicative of a relative importance of frequency bands for at least one token pair of the plurality of token pairs.

4. The method of claim 3, wherein:
   adjusting the one or more frequency channels entails adjusting the channels corresponding to those having relatively higher relative importance.

5. The method of claim 1, wherein:
   the obtained data is data indicative of a relative importance of frequency bands for at least one token pair having tokens conflated by the recipient of the plurality of token pairs.

6. The method of claim 1, wherein:
   the one or more frequency channels adjusted are channels corresponding to frequency bands having respective token pair relative spectral energies that are higher than other respective token pair relative spectral energies.

7. The method of claim 1, wherein:
   the obtained data is data based on respective signal strength data for respective frequency bands for specific tokens of the token pairs of the plurality of token pairs.

8. The method of claim 7, wherein:
   obtaining respective signal strength data for respective frequency bands entails evoking the hearing percepts utilizing a cochlear implant and utilizing a map to control the cochlear implant; and
   adjusting parameters of the hearing prosthesis based on identified frequency bands entails adjusting the map utilized to control the cochlear implant.

9. The method of claim 1, wherein:
   adjusting the one or more frequency channels entails increasing an output energy of the hearing prosthesis at that channel relative to that which was the case when the hearing percepts were evoked.

10. A method of fitting a hearing prosthesis, comprising:
    obtaining respective signal strength data for respective frequency bands for one or more first token pairs, the one or more first token pairs corresponding to hearing percepts evoked by the hearing prosthesis;
    identifying one or more frequency bands of a plurality of frequency bands for the one or more first token pairs where the respective signal strength data indicates relatively higher signal strength relative to that of one or more other frequency bands for the one or more token pairs; and
    adjusting parameters of the hearing prosthesis based on the identified frequency bands.

11. The method of claim 10, wherein the action of obtaining respective signal strength data entails:
    obtaining respective first signal strength data for a plurality of first frequency bands for a plurality of respective first tokens;
    obtaining respective signal strength differences between respective first signal strength data for two first tokens, thereby obtaining the respective signal strength data for the one or more first toke pairs.

12. The method of claim 11, wherein the action of obtaining respective first signal strength data entails a step for performing a function of creating a matrix having columns corresponding to the respective first frequency bands and rows corresponding to respective first tokens, the values of the matrix corresponding to the respective first signal strength data.

13. The method of claim 11, wherein the action of obtaining respective spectral energy differences entails:
    a step for performing a function of creating matrix based on absolute value differences between values of respective columns of the matrix for respective token pairs; and a step for performing a function of creating a vector having columns corresponding to the respective first frequency bands by subtracting rows of the obtained matrix corresponding to token pairs representing tokens correctly differentiated by the recipient from a sum of the rows of the obtained matrix corresponding to token pairs resenting tokens conflated by the recipient.

14. The method of claim 11, wherein obtaining respective spectral energy differences entails executing a step for performing a function of compiling data for the respective energy difference.

15. The method of claim 11, wherein the action of obtaining respective first signal strength data entails executing a step for performing a function of compiling the respective first signal strength data.

16. The method of claim 10, wherein the obtained respective signal strength data for the respective frequency bands for one or more first token pairs is based on a plurality of first token pairs, wherein at least one of the first token pairs represents tokens conflated by the recipient and wherein at least one other of the first token pairs represents tokens correctly differentiated by the recipient.

17. The method of claim 10, wherein:
the hearing prosthesis is a cochlear implant; and
adjusting parameters of the hearing prosthesis entails increasing a relative current level of one or more channels of the hearing prosthesis corresponding to identified one or more frequency bands, a percentage increase of the increase being greater than a percentage increase of any increase of non-identified frequency bands.

18. A non-transitory computer readable medium having recorded thereon, a computer program for executing a method, the computer program including:
code for manipulating frequency based data based on an ability of the recipient to correctly distinguish between tokens of a plurality of tokens, wherein the manipulated frequency based data is frequency based data for respective tokens of respectively evoked hearing percepts induced by a hearing prosthesis, the respective tokens making up the plurality of tokens; and
code for adjusting an output control of the hearing prosthesis with respect to one or more frequency bands of a plurality of frequency bands of the hearing prosthesis based on the manipulated data.

19. The medium of claim 18, wherein:
the frequency based data for respective tokens is for a plurality of token pairs of the tokens;
the frequency based data corresponds to respective signal strengths for respective frequency bands;
manipulating the frequency based data entails obtaining respective absolute value signal strength based data for the token pairs.

20. The medium of claim 19, wherein manipulating the frequency based data further entails merging the respective absolute value signal strength based data for the token pairs.

21. The medium of claim 20, wherein the action of merging the respective absolute value signal strength based data for the token pairs entails obtaining a discrete set of frequency band specific data by summing the absolute value signal strength based data for token pairs having tokens conflated by the recipient and discounting that summation by the absolute value signal strength based data for token pairs having tokens correctly discriminated by the recipient.

22. The medium of claim 18, wherein:
the frequency based data for respective tokens is for a plurality of token pairs of the tokens; and
manipulating the frequency based data entails mathematically manipulating the frequency based data to identify frequency bands that are relatively more important relative to other frequency bands for token pairs having tokens that were not correctly discriminated when the hearing percepts were evoked.

23. The medium of claim 22, wherein:
the frequency based data for respective tokens is for a plurality of token pairs of the tokens; and
manipulating the frequency based data entails mathematically manipulating the frequency based data to identify frequency bands that are relatively more important relative to other frequency bands for token pairs having tokens that were not correctly discriminated when the hearing percepts were evoked while discounting for token pairs having tokens that were correctly discriminated.

24. The medium of claim 22, wherein:
adjusting an output of the hearing prosthesis in one or more frequency bands of a plurality of frequency bands entails adjusting output controls in only some of the frequency bands of the plurality of frequency bands of the hearing prosthesis.

* * * * *